United States Patent
Seibel et al.

(10) Patent No.: US 10,513,532 B2
(45) Date of Patent: Dec. 24, 2019

(54) COMPOUND CONTAINING DEXPANTHENOL

(71) Applicant: JULIUS-MAXIMILIANS-UNIVERSITAET WUERZBURG, Wuerzburg (DE)

(72) Inventors: Juergen Seibel, Wuerzburg (DE); Malte Timm, Gerbrunn (DE)

(73) Assignee: Julius-Maximilians-Universitaet Wuerzburg, Wuerzburg (DE)

( * ) Notice: Subject to any disclaimer, the term of this patent is extended or adjusted under 35 U.S.C. 154(b) by 0 days.

(21) Appl. No.: 16/148,107

(22) Filed: Oct. 1, 2018

(65) Prior Publication Data

US 2019/0031699 A1    Jan. 31, 2019

Related U.S. Application Data

(63) Continuation of application No. PCT/EP2017/057038, filed on Mar. 24, 2017.

(30) Foreign Application Priority Data

Apr. 1, 2016 (DE) .......................... 10 2016 205 474

(51) Int. Cl.
*C07H 15/04* (2006.01)
*A61K 31/7032* (2006.01)
*A61K 8/60* (2006.01)
*A61Q 19/00* (2006.01)
*A61K 8/67* (2006.01)

(52) U.S. Cl.
CPC ............... *C07H 15/04* (2013.01); *A61K 8/60* (2013.01); *A61K 8/673* (2013.01); *A61K 31/7032* (2013.01); *A61Q 19/00* (2013.01); *A61Q 19/007* (2013.01)

(58) Field of Classification Search
None
See application file for complete search history.

(56) References Cited

PUBLICATIONS

PubChem record for Panthenyl ethyl ether, https://pubchem.ncbi.nlm.nih.gov/compound/Panthenyl-ethyl-ether, downloaded from the internet Aug. 15, 2019.*
Ebner F., et al.: "Topical use of dexpanthenol in skin disorders", American journal of clinical dermato, ADIS, US, Jan. 1, 2002.

* cited by examiner

*Primary Examiner* — Layla D Berry
(74) *Attorney, Agent, or Firm* — Laurence A. Greenberg; Werner H. Stemer; Ralph E. Locher (57) ABSTRACT

A compound contains a chemical dexpanthenol bound to a saccharide. A corresponding compound for use in therapeutic and/or cosmetic methods is also provided. The compound may be a skincare compound or a compound configured to be used in prophylaxis of skin diseases and/or treatment of skin diseases or a compound configured to be used as a medicament for accelerating wound healing.

12 Claims, 8 Drawing Sheets

COMPOUND CONTAINING DEXPANTHENOL

CROSS-REFERENCE TO RELATED APPLICATION

This is a continuation application, under 35 U.S.C. § 120, of copending international application No. PCT/EP2017/057038, filed Mar. 24, 2017, which designated the United States; this application also claims the priority, under 35 U.S.C. § 119, of German Patent Application DE 10 2016 205 474.0, filed Apr. 1, 2016; the prior applications are herewith incorporated by reference in their entirety.

BACKGROUND OF THE INVENTION

Field of the Invention

The invention relates to a compound containing dexpanthenol, which compound is especially suitable for use in therapeutic and/or cosmetic methods.

Human skin is the organ with the largest surface area of the human body, and serves as a "protective organ" for the human body. The skin adopts important roles in terms of metabolism and immunology and has many adaptation mechanisms.

The skin's most important function is its barrier function, that is protecting the organism from drying out. Healthy skin does not normally require any aids for retaining natural moisture, since skin moisture is regulated by "Natural Moisturizing Factors" (NMFs) in the epidermis, the uppermost layer of the skin, with these NMFs being constantly replenished as the skin is regenerated. However, environmental stresses, as well as dry air or exposure to UV radiation, contribute to removing moisture from the skin and/or destroying the natural moisturizing factors.

A deficient supply of moisture to the skin, especially with increasing age, may for example become apparent through pigmentation, wrinkle formation, slackening and inflammation of the skin. In the case of dry skin, wrinkles and microscopic fissures may for example form, into which germs penetrate, which may then lead to skin infections in the epidermis.

In order to prevent this, or in order to minimize the negative effects, creams and lotions with dexpanthenol as active ingredient are commonly used. Dexpanthenol is used for skincare and also for the topical treatment of skin diseases. Due to its hygroscopic properties, dexpanthenol improves the moisturization of the skin, decreases its roughness and serves to combat skin irritation and thus to indirectly sooth inflammation. Dexpanthenol has proved to be of value as a constituent of ointments, for example for superficial skin and mucous membrane damage, and also in foam sprays for treating first-degree burns. Furthermore, dexpanthenol stimulates cell growth and thus reduces the scar formation time of wounds.

However, dexpanthenol is rapidly absorbed by the skin and converted to pantothenic acid, also known as provitamin B5, via the blood circulation. The period of action of dexpanthenol after application to the skin is therefore limited in terms of time.

SUMMARY OF THE INVENTION

It is accordingly an object of the invention to provide a compound containing dexpanthenol, which overcomes the hereinafore-mentioned disadvantages of the heretofore-known compounds of this general type and which increases the period of action of dexpanthenol applied to the skin in the context of therapeutic and/or cosmetic methods.

With the foregoing and other objects in view there is provided, in accordance with the invention, a compound, comprising a dexpanthenol chemically bonded to a saccharide.

In a first step, the invention takes account of the fact that there are commercially available cosmetics, creams and also pharmaceutical agents in which the period of action is controlled by a delayed release of the active ingredients present. This is achieved for example by encapsulation, embedding or microencapsulation of the active ingredients present, since in this way the release of the active ingredient from the skincare product or the pharmaceutical agent is slowed down. In the case of skincare products, multiple emulsions are also used, in which both fat-soluble and water-soluble active ingredients enter the skin simultaneously and are released in succession. The action may be correspondingly lengthened by the delayed release of the active ingredients. In pharmaceutical agents, there are "retarding pharmaceutical forms", by means of which defined time profiles of release of the pharmaceutical substance can be achieved.

In a second step, the invention acknowledges that a delayed release of an active ingredient is especially achievable if the active ingredient is used as a glycoside. This is because such a glycoside, as described in more detail below, is only cleaved gradually in or on the body by naturally occurring enzymes, to release the active substance. In a third step, the invention applies this knowledge to the active ingredient dexpanthenol, by virtue of the latter not being used as an isolated molecule but rather in the form of a glycoside. The compound specified according to the invention is characterized by a dexpanthenol chemically bonded to a saccharide. Such a modification of dexpanthenol enables the desired delayed release of dexpanthenol active ingredient.

When the compound alone or as a constituent of a composition is applied to the skin, then the dexpanthenol is only released when the compound is cleaved, that is in a time-delayed manner. Thus, dexpanthenol only becomes effective as active ingredient after successful bond cleavage. In other words, the period of action of the dexpanthenol is lengthened depending on the cleavage of the chemically bonded saccharide.

The bond cleavage preferably occurs by reacting the compound with one or more enzymes. Advantageously, the compound is cleaved in the presence of glucosidases. Glucosidases are enzymes that are produced inter alia by bacteria and fungi that are naturally present on the skin. After applying the compound to the skin, the compound is cleaved, with release of dexpanthenol, by the glucosidases produced as enzymes by the bacteria and/or fungi; in other words therefore the bond between the dexpanthenol and the saccharide is broken.

In addition, according to our experiments, the compound of the dexpanthenol chemically bonded to a saccharide has increased polarity compared to pure dexpanthenol. This is accompanied by increased moisturization, that is the deposition of water molecules with formation of a hydration shell. Consequently, slowed penetration into the skin compared to pure dexpanthenol can be observed, which is a further advantage of the specified compound for the purpose of a lengthened period of action of dexpanthenol.

It is particularly preferred if the dexpanthenol and the saccharide are chemically bonded to one another via a glycosidic bond. Glycosidic bond is used to denote the chemical bond between the anomeric carbon atom of a glycone, i.e. a saccharide, and the heteroatom, or occasionally carbon atom, of an aglycone, a "non-sugar". Compounds comprising a glycosidic bond are generally referred to as glycosides. The hydrolysis of a glycosidic bond in a glycoside is especially reversibly catalyzed by glucosidases, with the glycone, in the present case the saccharide, and the aglycone, in this case dexpanthenol, being released with consumption of one molecule of water.

The saccharide is preferably a monosaccharide. Monosaccharides are simple sugars with a backbone of at least three linked carbon atoms, which have a carbonyl group (—C=O) and at least one hydroxyl group (—OH).

The monosaccharide is particularly preferably selected from a group comprising pentoses and hexoses. Hexoses ($C_6H_{12}O_6$) have a carbon backbone having six carbon atoms and differ from one another essentially by the type of carbonyl function. In the case of a carbonyl function not at the end ($R_1$—C(O)—$R_2$), a keto group, reference is made to ketohexoses. In the case of a carbonyl function at the end, an aldehyde group, these are aldohexoses. Pentoses ($C_5H_{10}O_5$) have a carbon backbone having five carbon atoms.

Hexoses are preferably selected from a group comprising α-glucose, β-glucose, α-fructose, β-fructose, α-mannose, β-mannose, α-galactose and β-galactose. Depending on which saccharide is chemically bonded to the dexpanthenol, the nomenclature of the compound is also different.

In the case of an α- or β-glucose chemically bonded to the dexpanthenol, the compound is α- or β-glycosylated dexpanthenol. In the case of an α- or β-galactose as chemically bonded saccharide, reference is made to α- or β-galactosylated dexpanthenol. If, as saccharide, an α- or β-fructose is bonded to the dexpanthenol, this is α- or β-fructosylated dexpanthenol.

The pentoses are advantageously selected from a group comprising arabinose and xylose.

In a particularly advantageous configuration of the invention, α-glucose is bonded to dexpanthenol via a glycosidic bond. The α-glycosylated dexpanthenol is synthesized from α-glucose and dexpanthenol with cleavage of water. This gives α-glycosylated dexpanthenol.

The compound is preferably characterized by the following structural formula:

In the synthesis of the α-glycosylated dexpanthenol, a glycosidic bond is formed between the α-glucose and the dexpanthenol. Particularly advantageously, the bonding occurs selectively at the hydroxyl group of the dexpanthenol that is bonded to the 1' carbon atom. The oxygen atom that connects the α-glucose to the dexpanthenol originates from the dexpanthenol. Essentially, this bond formation occurs—regardless of the saccharide used—preferably selectively at the hydroxyl group of the dexpanthenol that is bonded to the 1' carbon atom. In this case, the enzyme used for producing the glycoside is exclusively responsible for the selectivity of the bond formation.

The compound has a therapeutic and/or cosmetic action. In this respect, the compound is preferably provided for use in therapeutic and/or cosmetic methods. In this case, the compound serves, with delayed release of the dexpanthenol, for preventing skin damage and skin aging and also for caring for the skin.

The compound especially has a therapeutic and/or cosmetic action as a skincare product. Therefore, the compound is preferably provided for use in skincare. With protective application over a long period of time, the compound acts in a targeted manner against skin aging, or prevents same. The moisturizing action of dexpanthenol develops over a long period of time as a result of the lengthening of the period of action or the delayed release. Furthermore, dexpanthenol is able, in preventative use, to protect the skin from irritation. This effect is enhanced by a compound that releases dexpanthenol in a delayed manner.

Furthermore, the compound has a preventative action for avoiding skin diseases and/or for the treatment of skin diseases. Advantageously, therefore, the compound is provided for the prophylaxis of skin diseases and/or for the treatment of skin diseases. With consistent use of dexpanthenol, stabilization of the skin barrier is achieved through improved moisturization. In this way, by using dexpanthenol, the appearance of skin aging and changes to the skin can be prevented.

This includes for example eczematous changes to the skin such as xerotic eczema and stasis eczema with varicose veins, with cardiac and renal insufficiency and also with lymphatic edema, and also such as contact dermatitis. Furthermore, bacterial infections such as herpes zoster and shingles, fungal infections such as candida (yeast) infections of the skin and the mucous membranes, and also filamentous fungal infections can be prevented and/or treated. Similarly, dexpanthenol can be used to prevent and/or treat skin tumors, such as for example menorrheic keratoses ("senile warts"), actinic keratoses (precancerous), basal cell carcinomas (basaliomas) and squamous cell carcinomas.

Furthermore, the compound has a therapeutic action for accelerating wound healing. The compound is therefore particularly advantageously provided as medicament for accelerating wound healing. In 1992, S. Hauptmann, H. Schäfer, A. Fritz and P. Hauptmann published, in the journal "Der Hausarzt: Zeitschrift für Dermatologie, Venerologie and verwandte Gebiete" [*The Family Doctor: Journal of Dermatology, Venereology and Related Fields*], studies relating to the action of dexpanthenol on wound healing of human gingival fibroblasts in a concentration range from 0.5% to 10% in vitro. It was determined here that the mitotic index, the cell division index, was increased at all tested concentrations.

The best results were achieved with the lowest concentration of 0.5%, and the highest concentration of 10% effected the smallest action. In the context of the compound of a dexpanthenol chemically bonded to a saccharide, this means that dexpanthenol will now be provided in an effective, i.e. especially in a low, concentration over a long period of time in topical therapy for wound healing and cell regeneration.

Other features which are considered as characteristic for the invention are set forth in the appended claims.

Although the invention is illustrated and described herein as embodied in a compound containing dexpanthenol, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION (1) Preparation of α-glycosylated dexpanthenol Dexpanthenol (0.05 mol/l) and sucrose (0.4 mol/l) were dissolved in 0.05 M of phosphate buffer (0.05 mol/l, pH=6) and a suspension of microorganisms (*Protaminobacter rubrum* Z 12 (CBS 574.77)) was added thereto.

Sucrose consists of α-D-glucose and β-D-fructose, linked via an α,β-1,2-glycosidic bond. The microorganism *Protaminobacter rubrum* Z 12 contains an enzyme, an α-glucosidase. It catalyzes the cleavage of the sucrose used into α-D-glucose and β-D-fructose. During the reaction, the α-D-glucose bonds chemically to the dexpanthenol.

To this end, the reaction mixture is agitated in a water bath at a temperature of 37° C. After optimal product formation, the reaction is ended. The product, α-glycosylated dexpanthenol, is obtained in the form of a white solid in column chromatography analysis with EE-iPrOH—H$_2$O 6:3:1 as eluent. The optimal product formation is determined by continuous sampling and thin layer chromatography.

Figure 1:
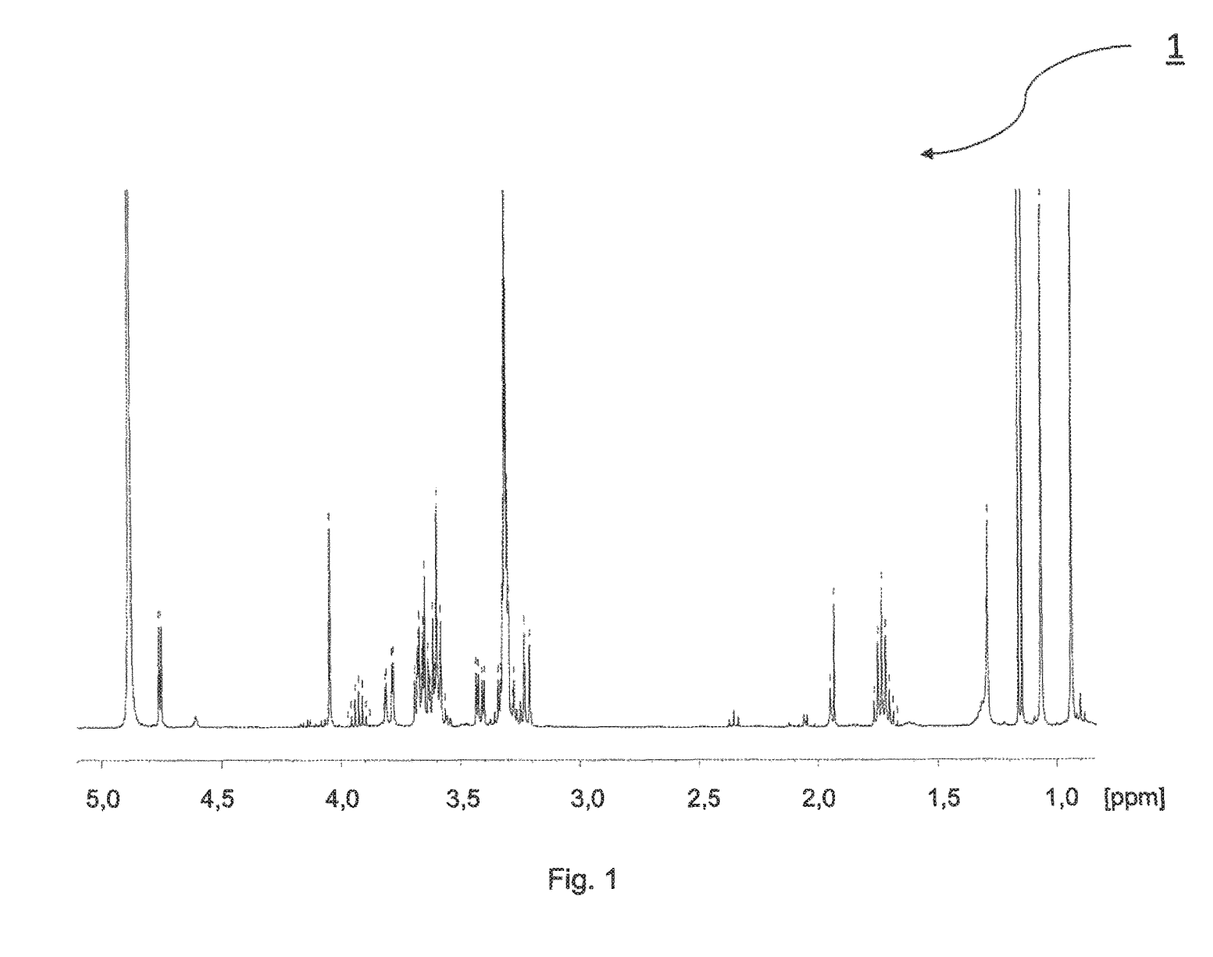
FIG. 1 is a diagram showing an exemplary $^1$H NMR spectrum of α-glycosylated dexpanthenol.

For the spectroscopic detection of the α-glycosylated dexpanthenol, $^1$H NMR and $^{13}$C NMR spectra were recorded. FIG. 1 shows an exemplary $^1$H NMR spectrum 1 of α-glycosylated dexpanthenol.

The $^1$H NMR spectrum 1 was recorded at 400 MHz in deuterated methanol and the signal assignment can be found in table 1.

TABLE 1

Signal assignment for the $^1$H NMR spectrum 1 of α-glycosylated dexpanthenol

| δ [ppm] | Assignment | Relative integral | Multiplicity | Coupling constant J [Hz] |
| --- | --- | --- | --- | --- |
| 4.76 | H-1 | 1H | Doublet | 3.7 |
| 4.05 | H-4' | 1H | Singlet | — |

TABLE 1-continued

Signal assignment for the $^1$H NMR spectrum 1 of α-glycosylated dexpanthenol

| δ [ppm] | Assignment | Relative integral | Multiplicity | Coupling constant J [Hz] |
| --- | --- | --- | --- | --- |
| 3.80 | H-6 | 1H | Doublet of doublets | 11.6; 2.2 |
| 3.69-3.58 | H-6b, H-3, H-1'a, H-4, H-8' | 6H | Multiplet | — |
| 3.42 | H-2 | 1H | Doublet of doublets | 9.6; 3.7 |
| 3.34-3.27 | 3 H, H-6', H-5 | 3H | Multiplet | — |
| 3.22 | H-1'b | 1H | Doublet | 9.1 |
| 1.77-1.68 | 2 H, H-7' | 2H | Multiplet | — |
| 1.07, 0.94 | H-3'a, H-3'b | 6H | Singlet | — |

Figure 2:
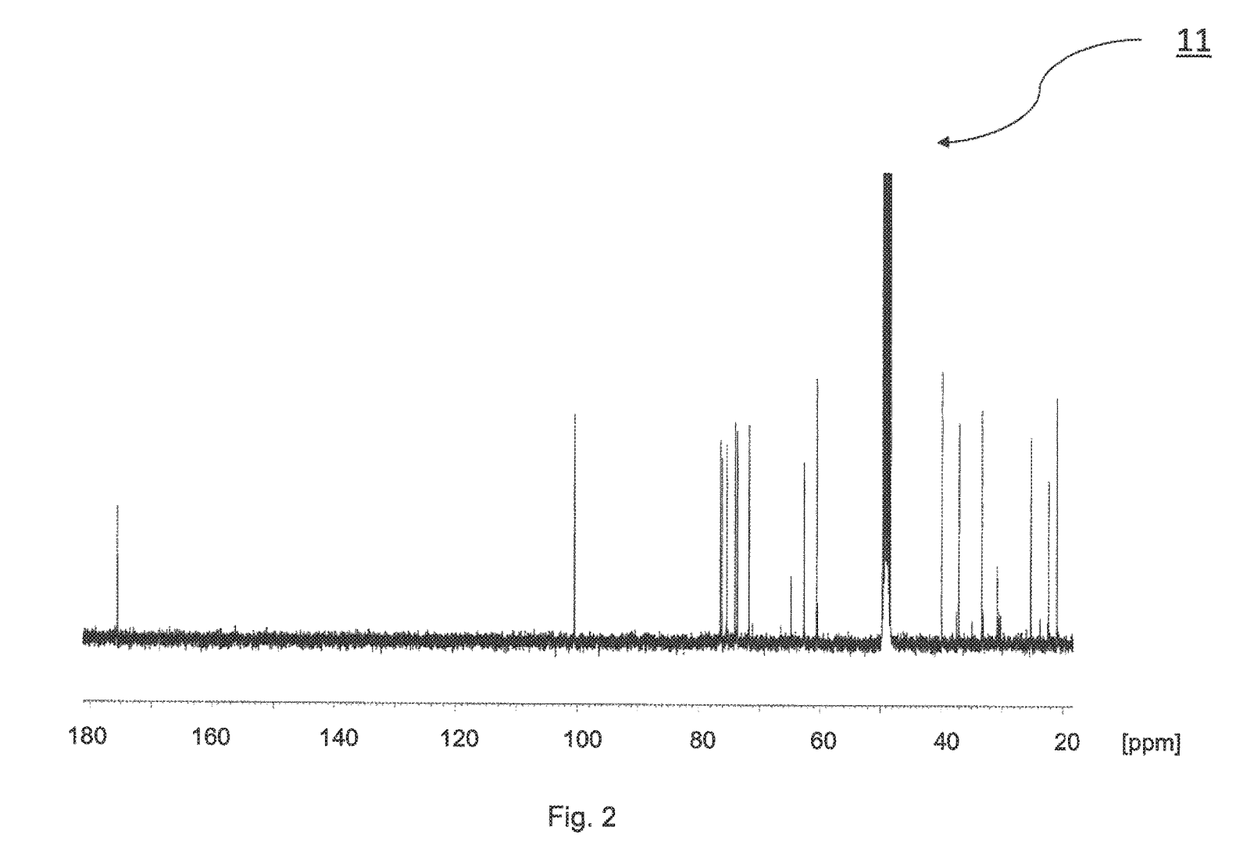
FIG. 2 is a diagram showing an exemplary $^{13}$C NMR spectrum of α-glycosylated dexpanthenol.

FIG. 2 shows an exemplary $^{13}$C NMR spectrum 11 of α-glycosylated dexpanthenol. The $^{13}$C NMR spectrum 11 was recorded at 100 MHz, also in deuterated methanol. The signal assignment is listed in table 2.

TABLE 2

Signal assignment for the $^{13}$C NMR spectrum 11 of α-glycosylated dexpanthenol

| δ[ppm] | Assignment |
| --- | --- |
| 176.65 | C-5' |
| 100.47 | C-1 |
| 76.41 | C-4' |
| 76.14 | C-1' |
| 75.30 | C-3 |
| 73.96 | C-4 |
| 73.59 | C-2 |
| 71.68 | C-5 |
| 62.61 | C-6 |
| 60.54 | C-8' |
| 39.89 | C-2' |
| 37.07 | C-6' |
| 33.33 | C-7' |
| 22.35, 21.00 | C-3'a, C-3'b |

The α-glucosylated dexpanthenol is unambiguously identified from the chemical shifts found in each of the tables of the signals of the H atoms and C atoms and the integral values (for the H atoms).

(2) Preparation of β-glucosylated dexpanthenol

Dexpanthenol (0.05 mol/l) and cellobiose (0.4 mol/l) were dissolved in sodium acetate buffer (0.05 mol/l, pH=5.2) and a β-glucosidase solution (100 U in sodium acetate buffer, β-glucosidase from almonds, BioChemika 49290, CAS 9001-22-3) was added thereto. Cellobiose is a disaccharide of two glucose molecules β-1,4-glucosidically linked to one another. The enzyme β-glucosidase enables the breakdown of cellobiose to give glucose. During the reaction, the glucose bonds chemically to the dexpanthenol.

The reaction mixture is likewise agitated in a water bath at a temperature of 37° C. After optimal product formation, the reaction is ended. The product, β-glucosylated dexpanthenol, is obtained in the form of a white solid in column chromatography analysis with EE-iPrOH—H$_2$O 6:3:1 as eluent.

Figure 3:
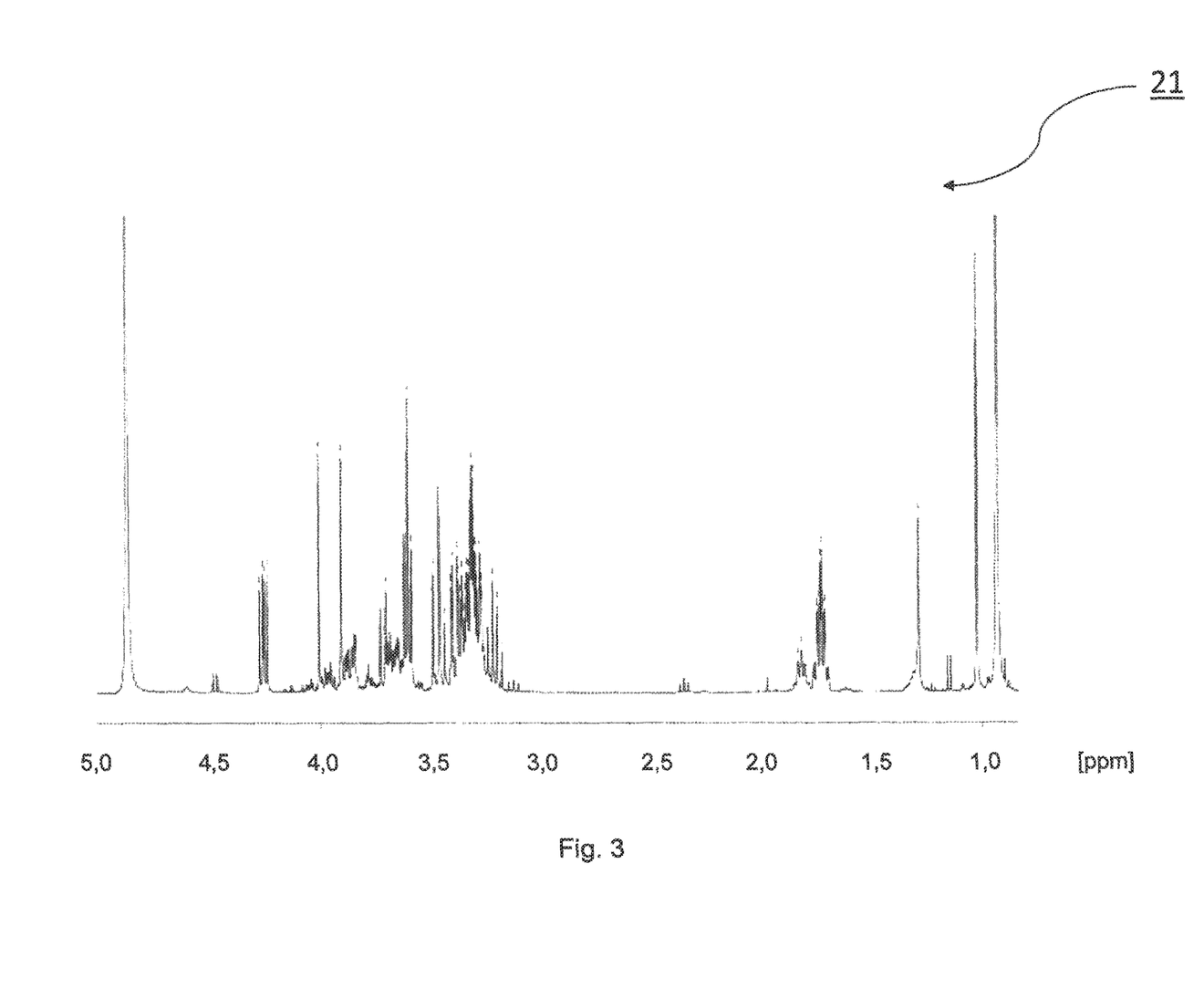
FIG. 3 is a diagram showing an exemplary $^1$H NMR spectrum of β-glucosylated dexpanthenol.

For the spectroscopic detection of the β-glucosylated dexpanthenol, $^1$H NMR and $^{13}$C NMR spectra were recorded. FIG. 3 shows an exemplary $^1$H NMR spectrum 21 of β-glucosylated dexpanthenol. The glucosylation products 2a and 2b are formed in this reaction.

2a

2b

The ¹H NMR spectrum 21 was recorded at 400 MHz in deuterated methanol and the signal assignment can be found in the following tables 3a and 3b.

TABLE 3a

Signal assignment for the ¹H NMR spectrum 21 of β-glucosylated dexpanthenol- linked via C-1'O

| δ [ppm] | Assignment | Relative integral | Multiplicity | Coupling constant J [Hz] |
|---|---|---|---|---|
| 4.25 | H-1 | 1H | Doublet | 7.8 |
| 4.01 | H-4' | 1H | Singlet | — |
| 3.83-3.89, 3.63-3.67 | H-6 | 2H | Multiplet | — |
| 3.61 | H-8' | 2H | Triplet | 6.2 |
| 3.72, 3.44 | H-1' | 2H | Two doublets | 9.1; 9.1 |
| 3.20-3.40 | H-3, H-4, H-5 | 3H | Multiplet | — |
| 3.29-3.36 | H-6' | 2H | Multiplet | — |
| 3.22 | H-2 | 1H | Multiplet | — |
| 1.73 | H-7' | 2H | Two quintets | 6.5; 2.1 |
| 1.03, 0.94 | H-3'a, H-3'b | 6H | Singlet | — |

TABLE 3b

Signal assignment for the ¹H NMR spectrum 21 of β-glucosylated dexpanthenol - linked via C-8'O

| δ [ppm] | Assignment | Relative integral | Multiplicity | Coupling constant J [Hz] |
|---|---|---|---|---|
| 4.26 | H-1 | 1H | Doublet | 7.8 |
| 3.91 | H-4' | 1H | Singlet | — |
| 3.83-3.89, 3.63-3.67 | H-6 | 2H | Multiplet | — |
| 3.61-3.65 | H-8' | 2H | Multiplet | — |
| 3.37-3.50 | H-1' | 2H | Multiplet | — |
| 3.20-3.40 | H-3, H-4, H-5 | 3H | Multiplet | — |
| 3.29-3.36 | H-6' | 2H | Multiplet | — |
| 3.20 | H-2 | 1H | Multiplet | — |
| 1.73 | H-7' | 2H | Two quintets | 6.5; 2.1 |
| 1.02, 0.94 | H-3'a, H-3'b | 6H | Singlet | — |

Figure 4:
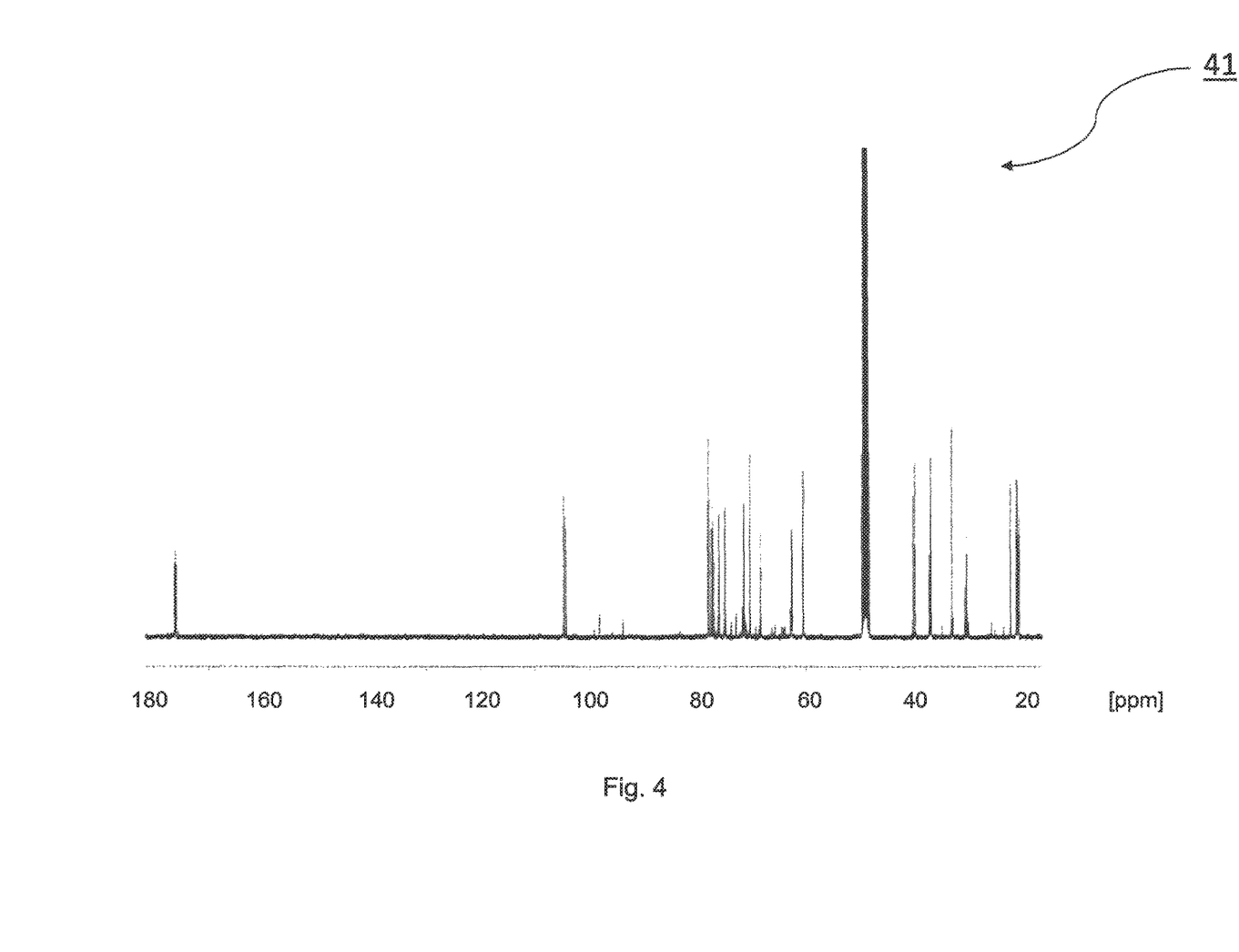
FIG. 4 is a diagram showing an exemplary $^{13}$C NMR spectrum of β-glucosylated dexpanthenol.

FIG. 4 shows the ¹³C NMR spectrum 41 of β-glucosylated dexpanthenol. The ¹³C NMR spectrum 41 was recorded at 100 MHz, also in deuterated methanol. The signal assignment is listed in tables 4a and 4b.

TABLE 4a

Signal assignment for the ¹³C NMR spectrum 41 of β-glucosylated dexpanthenol - linked via C-1'O

| δ[ppm] | Assignment |
|---|---|
| 176.15 | C-5' |
| 104.72 | C-1 |
| 77.11 | C-1' |
| 76.06 | C-4' |
| 77.95 | C-3 |
| 77.93 | C-4 |
| 75.01 | C-2 |
| 71.57 | C-5 |
| 60.56 | C-8' |
| 60.52 | C-6 |
| 39.91 | C-2' |
| 37.03 | C-6' |
| 33.19 | C-7' |
| 22.34, 21.31 | C-3'a, C-3'b |

TABLE 4b

Signal assignment for the ¹³C NMR spectrum 41 of β-glucosylated dexpanthenol - linked via C-8'O

| δ[ppm] | Assignment |
|---|---|
| 175.94 | C-5' |
| 104.32 | C-1 |
| 78.02 | C-3 |
| 77.39 | C-4' |
| 77.31 | C-4 |
| 75.05 | C-2 |
| 71.52 | C-5 |
| 70.34 | C-1' |
| 68.43 | C-8' |
| 62.62 | C-6 |
| 40.34 | C-2' |
| 37.27 | C-6' |
| 30.39 | C-7' |
| 21.36, 20.83 | C-3'a, C-3'b |

The β-glucosylated dexpanthenol is unambiguously identified from the chemical shifts found in each of the tables of the signals of the H atoms and C atoms and the integral values (for the H atoms).

(3) Preparation of β-galactosylated dexpanthenol

Dexpanthenol (0.05 mol/l) and lactose (0.4 mol/l) were dissolved in sodium acetate buffer (0.05 mol/l, pH=5.2) and a β-galactosidase solution (100 U in sodium acetate buffer, β-galactosidase from *Aspergillus oryzae*, Sigma G5160, CAS 9031-11-2) was added thereto. Lactose consists of D-galactose and D-glucose bonded via a β-1,4-glycosidic bond. β-galactosidases enzymatically catalyse the hydrolysis of this bond, with galactose being formed, which bonds chemically to the dexpanthenol during the reaction.

To this end, the reaction mixture is agitated in a water bath at a temperature of 37° C. After optimal product formation, the reaction is ended. The product, β-galactosylated dexpanthenol, is obtained in the form of a white solid in column chromatography analysis with EE-iPrOH—H₂O 6:3:1 as eluent.

Figure 5:
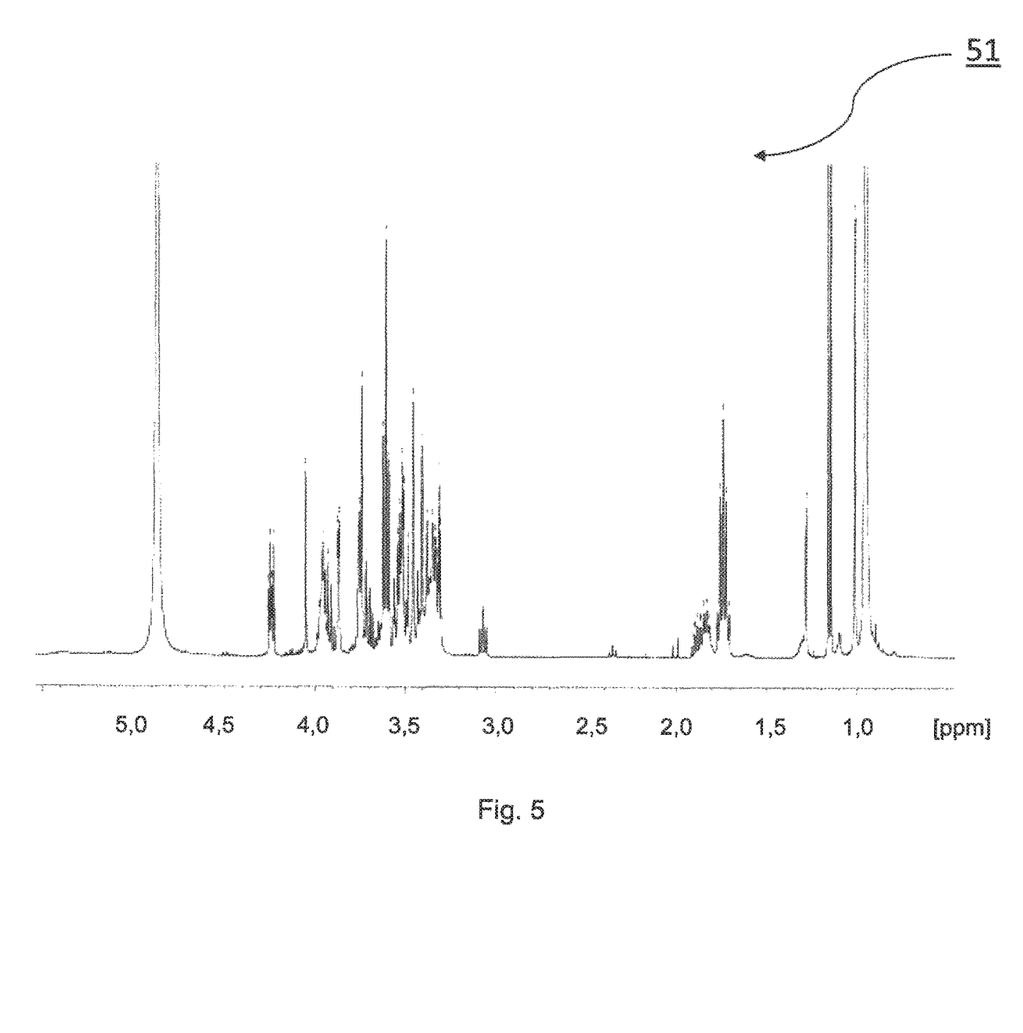
FIG. 5 is a diagram showing an exemplary $^1$H NMR spectrum of β-galactosylated dexpanthenol.

For the spectroscopic detection of the β-galactosylated dexpanthenol, ¹H NMR and ¹³C NMR spectra were recorded. FIG. 5 shows an exemplary ¹H NMR spectrum of β-galactosylated dexpanthenol. The following galactosylation products 3a and 3b are formed in this reaction.

3a

3b

The ¹H NMR spectrum 51 was recorded at 400 MHz in deuterated methanol and the signal assignment can be found in the tables 5a and 5b.

TABLE 5a

Signal assignment for the ¹H NMR spectrum 51 of β-galactosylated dexpanthenol - linked via C-1'O

| δ [ppm] | Assignment | Relative integral | Multiplicity | Coupling constant J [Hz] |
|---|---|---|---|---|
| 4.24 | H-1 | 1H | Doublet | 7.8 |
| 4.05 | H-4' | 1H | Singlet | — |
| 3.92-3.97 | H-5 | 1H | Multiplet | — |
| 3.86-3.88 | H-3 | 1H | Multiplet | — |
| 3.74-3.76 | H-6 | 2H | Multiplet | — |
| 3.74-3.76, 3.51-3.56 | H-1' | 2H | Multiplet | — |
| 3.61 | H-8' | 2H | Triplet | 6.2 |
| 3.51 | H-2 | 1H | Multiplet | — |
| 3.48-3.51 | H-4 | 1H | Multiplet | — |
| 3.31-3.37 | H-6' | 2H | Multiplet | — |
| 1.74 | H-7' | 2H | Quintet | 6.4 |
| 1.01, 0.95 | H-3'a, H-3'b | 6H | Singlet | — |

TABLE 5b

Signal assignment for the ¹H NMR spectrum 51 of β-galactosylated dexpanthenol - linked via C-8'O

| δ [ppm] | Assignment | Relative integral | Multiplicity | Coupling constant J [Hz] |
|---|---|---|---|---|
| 4.25 | H-1 | 1H | Doublet | 7.8 |
| 3.95 | H-4' | 1H | Singlet | — |
| 3.92-3.97 | H-5 | 1H | Multiplet | — |
| 3.86-3.88 | H-3 | 1H | Multiplet | — |
| 3.74-3.76 | H-6 | 2H | Multiplet | — |
| 3.63, 3.96 | H-8' | 2H | Multiplet | — |
| 3.51-3.56 | H-2 | 1H | Multiplet | — |
| 3.48-3.52 | H-4 | 1H | Multiplet | — |
| 3.39, 3.47 | H-1' | 2H | 2 doublets | 11.1; 11.4 |
| 3.35 | H-6' | 2H | Multiplet | — |
| 1.83 | H-7' | 2H | Multiplet | — |
| 1.01, 0.95 | H-3'a, H-3'b | 6H | Singlet | — |

Figure 6:
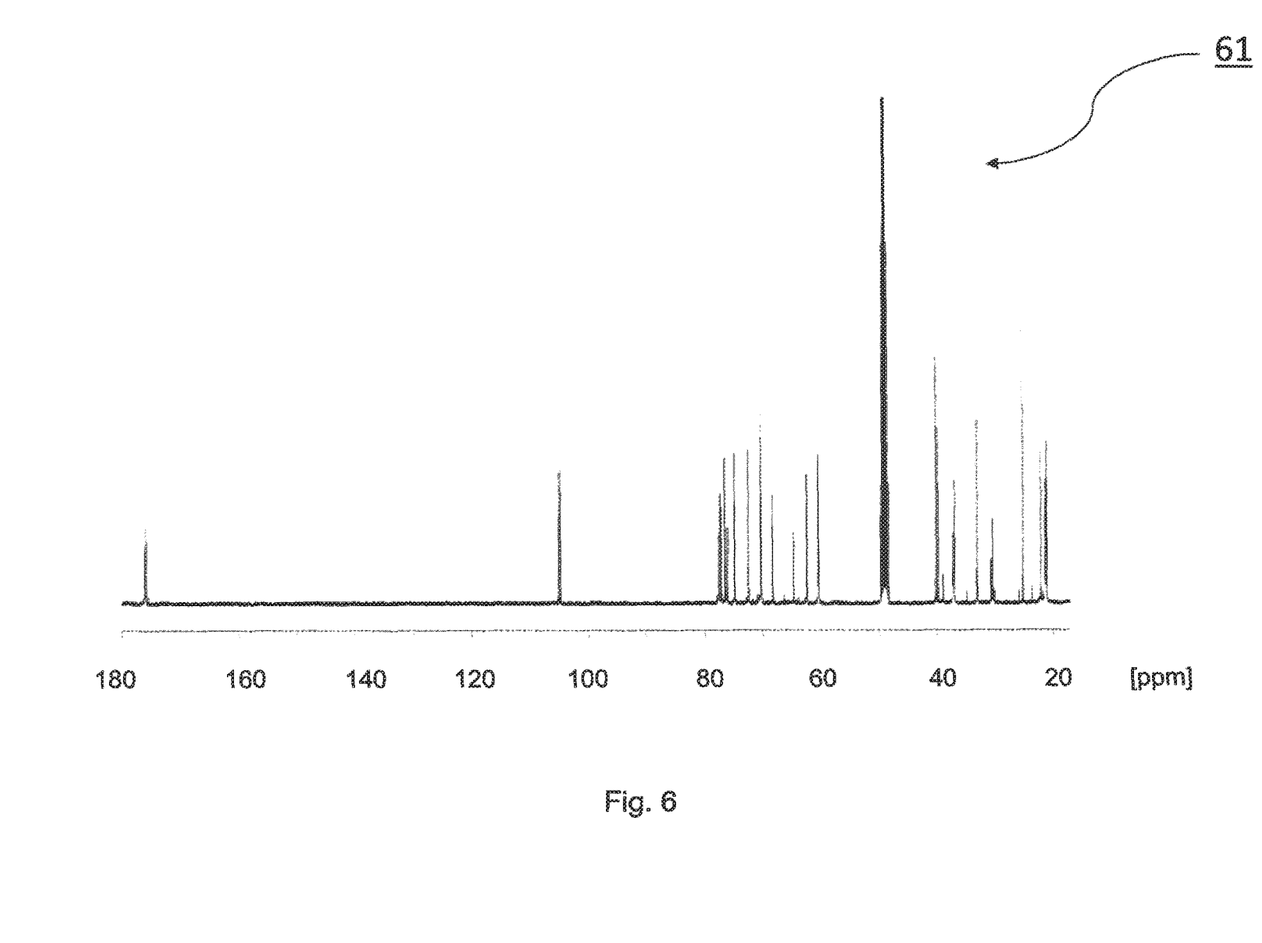
FIG. 6 is a diagram showing an exemplary $^{13}$C NMR spectrum of β-galactosylated dexpanthenol.

FIG. 6 shows the ¹³C NMR spectrum 61 of β-galactosylated dexpanthenol. The ¹³C NMR spectrum 61 was recorded at 100 MHz, also in deuterated methanol. The signal assignment is listed in tables 6a and 6b.

TABLE 6a

Signal assignment for the ¹³C NMR spectrum 61 of β-galactosylated dexpanthenol - linked via C-1'O

| δ[ppm] | Assignment |
|---|---|
| 176.15 | C-5' |
| 105.20 | C-1 |
| 77.44 | C-5 |
| 76.97 | C-1' |
| 76.52 | C-2 |
| 76.44 | C-5 |
| 76.11 | C-4' |
| 70.30 | C-3 |
| 62.40 | C-6 |
| 60.37 | C-8' |
| 39.84 | C-2' |
| 37.01 | C-6' |
| 33.08 | C-7' |
| 22.11, 21.15 | C-3'a, C-3'b |

TABLE 6b

Signal assignment for the ¹³C NMR spectrum 61 of β-galactosylated dexpanthenol - linked via C-8'O

| δ[ppm] | Assignment |
|---|---|
| 175.92 | C-5' |
| 104.82 | C-1 |
| 77.51 | C-4' |
| 77.44 | C-5 |
| 76.46 | C-4 |
| 72.46 | C-2 |
| 70.35 | C-3 |
| 70.21 | C-1' |
| 68.30 | C-8' |
| 62.39 | C-6 |
| 40.27 | C-2' |
| 37.03 | C-6' |
| 30.45 | C-7' |
| 21.31, 21.40 | C-3'a, C-3'b |

The β-galactosylated dexpanthenol is unambiguously identified from the chemical shifts found in each of the tables of the signals of the H atoms and C atoms and the integral values (for the H atoms).

(4) Preparation of fructosylated dexpanthenol

Dexpanthenol (0.05 mol/l) and sucrose (0.4 mol/l) were dissolved in sodium acetate buffer (0.05 mol/l, pH=5.2) and a fructosidase solution (100 U in sodium acetate buffer, Boehringer Mannheim GmbH, β-fructosidase from yeast, reference number 104914) was added thereto. The fructosidase solution enzymatically catalyses the cleavage of the sucrose into α-D-glucose and β-D-fructose. During the reaction, the β-D-fructose bonds chemically to the dexpanthenol.

Figure 7:
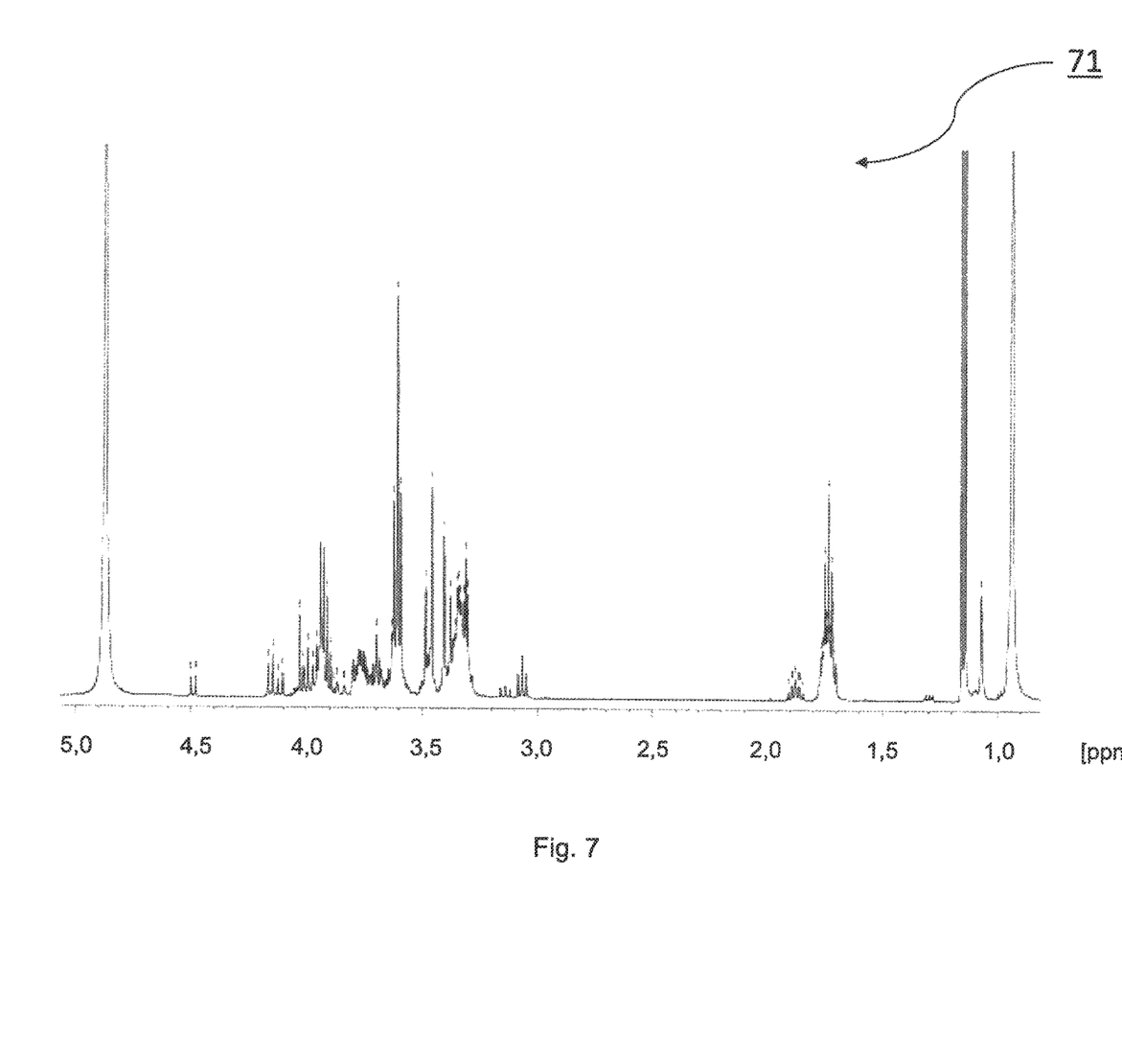
FIG. 7 is a diagram showing an exemplary $^1$H NMR spectrum of fructosylated dexpanthenol.
Figure 8:
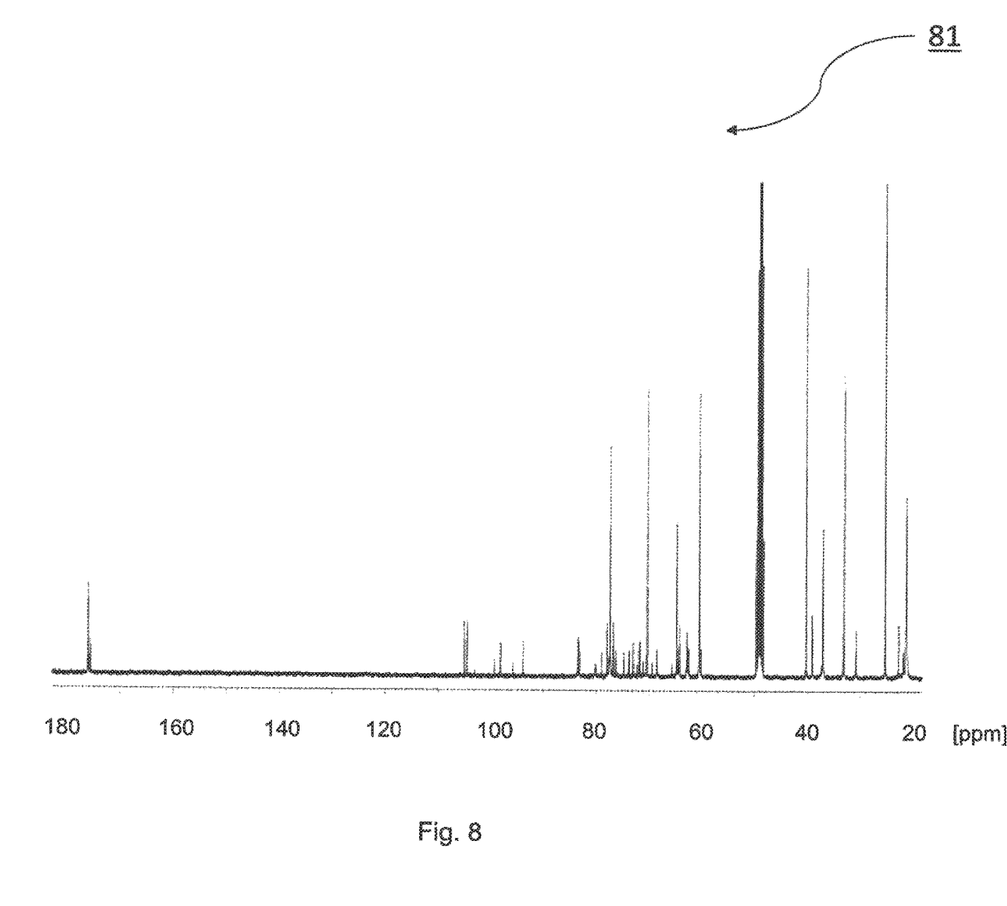
FIG. 8 is a diagram showing an exemplary $^{13}$C NMR spectrum of fructosylated dexpanthenol.

To this end, the reaction mixture is also agitated in a water bath at a temperature of 37° C. After optimal product formation, the reaction is ended. The product, fructosylated dexpanthenol, is obtained in the form of a white solid in column chromatography analysis with EE-iPrOH—H₂O 6:3:1 as eluent. The product, fructosylated dexpanthenol, has the following structural formula For the spectroscopic detection of the fructosylated dexpanthenol, $^1$H NMR and $^{13}$C NMR spectra were also recorded. FIG. 7 shows an exemplary $^1$H NMR spectrum 71 of fructosylated dexpanthenol. FIG. 8 shows an exemplary $^{13}$C NMR spectrum 81 of fructosylated dexpanthenol. The conjugated product of fructose and dexpanthenol is found from the signals of the spectra 71, 81. The signal assignment is found in tables 7 and 8.

TABLE 7

| δ [ppm] | Assignment | Relative integral | Multiplicity | Coupling constant J [Hz] |
| --- | --- | --- | --- | --- |
| 4.16 | H-3 | 1H | Doublet | 8.9 |
| 4.03 | H-4' | 1H | Singlet | |
| 4.00 | H-4 | 1H | Triplet | 8.9 |
| 3.76 | H-5 | 1H | Multiplet | |
| 3.61 | H-1, H-6, H-8' | 6H | Multiplet | |
| 3.47 | H-1' | 2H | Multiplet | |
| 3.34 | H-6' | 2H | Multiplet | |
| 1.73 | H-7' | 2H | Multiplet | |
| 1.07 | H-3' | 6H | Singlet | |

TABLE 8

| δ[ppm] | Assignment |
| --- | --- |
| 175.65 | C-5' |
| 104.43 | C-2 |
| 83.52 | C-5 |
| 80.07 | C-3 |
| 77.44 | C-4' |
| 76.67 | C-4 |
| 77.44 | C-4' |
| 68.40 | C-1' |
| 64.17 | C-6 |
| 63.80 | C-1 |
| 60.59 | C-8' |
| 39.13 | C-2' |
| 37.03 | C-6' |
| 33.14 | C-7' |
| 20.74 | 2 × C-3' |

The fructosylated dexpanthenol is unambiguously identified from the chemical shifts found in each of the tables 7 and 8 of the signals of the H atoms and C atoms and the integral values (for the H atoms).

The following is a summary list of reference numerals and the corresponding structure used in the above description of the invention:

LIST OF REFERENCE NUMERALS

1 $^1$H NMR spectrum of α-glucosylated dexpanthenol
11 $^{13}$C NMR spectrum of α-glucosylated dexpanthenol
21 $^1$H NMR spectrum of β-glucosylated dexpanthenol
41 $^{13}$C NMR spectrum of β-glucosylated dexpanthenol
51 $^1$H NMR spectrum of β-galactosylated dexpanthenol
61 $^{13}$C NMR spectrum of β-galactosylated dexpanthenol
71 $^1$H NMR spectrum of β-fructosylated dexpanthenol
81 $^{13}$C NMR spectrum of β-fructosylated dexpanthenol

The invention claimed is:

1. A compound, comprising a dexpanthenol chemically bonded to a saccharide.

2. The compound according to claim 1, wherein the dexpanthenol and the saccharide are chemically bonded to one another by a glycosidic bond.

3. The compound according to claim 1, wherein the saccharide is a monosaccharide.

4. The compound according to claim 3, wherein the monosaccharide is selected from the group consisting of hexoses and pentoses.

5. The compound according to claim 4, wherein the hexoses are selected from the group consisting of α-glucose, β-glucose, α-fructose, β-fructose, α-galactose and β-galactose, α-mannose and β-mannose.

6. The compound according to claim 4, wherein the pentoses are selected from the group consisting of arabinose and xylose.

7. The compound according to claim 5, wherein the α-glucose is bonded to the dexpanthenol by a glycosidic bond.

8. The compound according to claim 1, wherein the compound has the following structural formula:

9. The compound according to claim 1, wherein the compound is at least one of a therapeutic or cosmetic compound.

10. The compound according to claim 1, wherein the compound is a skincare compound.

11. The compound according to claim 1, wherein the compound is configured to be used in at least one of prophylaxis of skin diseases or treatment of skin diseases.

12. The compound according to claim 1, wherein the compound is configured to be used as a medicament for accelerating wound healing.

\* \* \* \* \*